(12) United States Patent
Larsen et al.

(10) Patent No.: US 9,758,843 B2
(45) Date of Patent: Sep. 12, 2017

(54) METHOD OF PROCESSING LIGNOCELLULOSIC BIOMASS USING FEEDBACK CONTROL OF HYDROTHERMAL PRETREATMENT

(71) Applicant: INBICON A/S, Fredericia (DK)

(72) Inventors: Jan Larsen, Toramerup (DK); Kit Kellebjerg Mogensen, Fredericia (DK); Pia Jørgensen, Kolding (DK)

(73) Assignee: INBICON A/S, Fredericia (DK)

( * ) Notice: Subject to any disclaimer, the term of this patent is extended or adjusted under 35 U.S.C. 154(b) by 0 days.

(21) Appl. No.: 14/378,332

(22) PCT Filed: Jan. 16, 2013

(86) PCT No.: PCT/DK2013/000006
§ 371 (c)(1),
(2) Date: Aug. 13, 2014

(87) PCT Pub. No.: WO2013/120492
PCT Pub. Date: Aug. 22, 2013

(65) Prior Publication Data
US 2015/0128933 A1    May 14, 2015

Related U.S. Application Data

(60) Provisional application No. 61/586,844, filed on Feb. 15, 2012.

(51) Int. Cl.
| | | |
|---|---|---|
| *C13K 13/00* | (2006.01) | |
| *C12P 19/02* | (2006.01) | |
| *C12P 19/14* | (2006.01) | |
| *C12P 7/10* | (2006.01) | |

(52) U.S. Cl.
CPC ............. *C13K 13/002* (2013.01); *C12P 7/10* (2013.01); *C12P 19/02* (2013.01); *C12P 19/14* (2013.01); *C12P 2201/00* (2013.01); *Y02E 50/16* (2013.01)

(58) Field of Classification Search
None
See application file for complete search history.

(56) References Cited

FOREIGN PATENT DOCUMENTS

| | | |
|---|---|---|
| JP | 63-159514 A | 12/1986 |
| JP | 2005-500410 A | 1/2005 |
| WO | WO 03/011912 A1 | 2/2003 |

OTHER PUBLICATIONS

Dilute-Sulfuric Acid Pretreatment of Corn Stover in Pilot-Scale Reactor Daniel J. Schell et al Applied Biochemistry and Biotechnology vol. 105-108, pp. 69-85, 2003.*

Influence of Xylan on the Enzymatic Hydrolysis of Steam-Pretreated Corn Stover and Hybrid Poplar Renata Bura Biotechnology Progress vol. 25, No. 2, pp. 315-322, 2009.*

Impact of corn stover composition on hemicellulose conversion during dilute acid pretreatment and enzymatic cellulose digestibility of the pretreated solids Noah D. Weiss et al. Bioresource Technology, vol. 101, pp. 674-678, 1010.*

The enhancement of enzymatic hydrolysis of lignocellulosic substrates by the addition of accessory enzymes such as xylanase: is it an additive or synergistic effect? Jinguang Hu et al. Biotech. for Biofuels, v 4:36, pp. 1-13, 2011.*

Alvira, P., et al., "Pretreatment technologies for an efficient bioethanol production process based on enzymatic hydrolysis: A review," *Bioresource Technology*, 2010, pp. 4851-4861, vol. 101 Elsevier Ltd.

Belkacemi, K., et al., "Phenomenological Kinetics of Complex Systesms: Mechanistic Considerations in the Solubilization of Hemicelluloses following Aqueous/Steam Treatments", *Ind. Eng. Chem. Res.*, 1991, pp. 2416-2425, vol. 30, No. 11, American Chemical Society.

Bura, R., et al., "Influence of Xylan on the Enzymatic Hydrolysis of Steam-Pretreated Corn Stover and Hybrid Poplar", *Biotechnol. Prog.*, 2009, pp. 315-320, vol. 25, No. 2, American Institute of Chemical Engineers.

Chandra, R. P., et al., "Substrate Pretreatment: The Key to Effective Enzymatic Hydrolysis of Lignocellulosics?", *Adv. Biochem Engin/Biotechnol*, 2007, pp. 67-93, vol. 108, Springer-Verlag.

Gollapalli, L. E., et al., "Predicting Digestibility of Ammonia Fiber Explosion (AFEX)-Treated Rice Straw", *Applied Biochemistry and Biotechnology*, 2002, pp. 23-35, vols. 98-100, Human Press Inc.

Hames, B. R., et al., "Rapid Biomass Analysis: New Tools for Compositional Analysis of Corn Stover Feedstocks and Process Intermediates from Ethanol Production", *Applied Biochemistry and Biotechnology*, 2003, pp. 5-16, vols. 105-108, Humana Press Inc.

Jacobsen, S. E., et al., "Cellulose and Hemicellulose Hydrolysis Models for Application to Current and Novel Pretreatment Processes", *Applied Biochemistry and Biotechnology*, 2000, pp. 81-96, vols. 84-86, Humana Press Inc.

Jeoh, T., et al., "Cellalose Digestibility of Pretreated Biomass in Limited Cellulose Accessibility", *Biotechnology and Bioengineering*, 2007, pp. 112-122, vol. 98, No. 1, Wiley Periodicals, Inc.

Kabel, M. A., et al, "Effect of Pretreatment Severity on Xylan Solubility and Enzymatic Breakdown of the Remaining Cellulose from Wheat Straw", Bioresource Technology, 2007, pp. 2034-2042, vol. 98, Elsevier Ltd.

(Continued)

*Primary Examiner* — Douglas B Call
(74) *Attorney, Agent, or Firm* — Womble Carlyle Sandridge & Rice LLP

(57) ABSTRACT

The invention relates to a method of processing lignocellulosic biomass comprising: providing lignocellulosic biomass feedstock; pretreating said biomass feedstock by continuous hydrothermal pretreatment in a pressurized reactor; measuring xylan number or lignin number in the output stream of pretreated biomass from the pretreatment reactor; and controlling the pretreatment reactor so as to maintain, in the output stream of pretreated biomass, a pre-determined level of measured xylan number or lignin number. The method allows for continuously controlling the digestibility of a lignocellulosic biomass during the step of pretreatment, and accordingly provides a continuous estimate of the severity of the pretreatment.

14 Claims, 9 Drawing Sheets

(56) References Cited

OTHER PUBLICATIONS

Knudsen, N. O., et al., "Possibilities and Evaluation of Straw Pretreatment", 10th European Biomass Conference in Würzburg in 1998, *Biomass for Energy and Industry*, pp. 224-228, C.A.R.M.A.N.

Larsen, J., et al., "Inbicon makes lignocellulosic ethanol a commercial reality", *Biomass and Bioenergy*, 2012, pp. 36-45, vol. 46, Elsevier Ltd.

Lindedam, J., et al., "Cellulosic ethanol: interactions between cultivar and enzyme loading in wheat straw processing", *Biotechnology for Biofuels*, 2010, pp. 1-10, vol. 3, No. 25, BioMed Central.

Liu, L., et al., "Variability of biomass composition and rapid analysis using FT-NIR techniques", *Carbohydrate Polymers*, 2010, pp. 820-829, vol. 81, Elsevier Ltd.

Lloyd, T. A., "Application of a Depolymerization Model for Predicting Thermochemical Hydrolysis of Hemicellulose", *Applied Biochemistry and Biotechnology*, 2003, pp. 53-67, vol. 105-108, Humana Press Inc.

Overend, R. P., et al., "Fractionation of lignocellulosics by steam-aqueous pretreatments", *Philos. Trans. R. Soc. Lond.*, 1987, pp. 523-536, vol. A 321, Royal Society Publishing.

Pérez, J. A., et al., "Effect of process variables on liquid hot water pretreatment of wheat straw for bioconversion to fuel-ethanol in a batch reactor", *Journal of Chemical Technology and Biotechnology*, 2007, pp. 929-938, vol. 82, Wiley.

Petersen, M., et al., "Optimization of hydrothermal pretreatment of wheat straw for production of bioethanol at low water consumption without addition of chemicals," *Biomass and Bioenergy*, 2009, pp. 834-840, vol. 33, Elsevier Ltd.

Sluiter, A., et al, "Determination of Structural Carbohydrates and Lignin in Biomass", US National Renewal Energy Laboratory Analytical Procedure with issue date Apr. 2008, as described in Technical Report NREL/TP-510-42618, revised Aug. 2012, 18 pages, NREL, USA.

Sluiter, A., et al., "Determination of Structural Carbohydrates and Lignin in Biomass," US National Renewal Energy Laboratory Analytical Procedure with issue date Apr. 2008, as described in Technical Report NREL/TP-510-42618, revised Jul. 2011, 18 pages, NREL, USA.

Sluiter, A., et al., "Determination of Sugars, Byproducts, and Degradation Products in Liquid Fraction Process Samples", US National Renewal Energy Laboratory Analytical Procedure with issue date Dec. 8, 2006, as described in Technical Report NREL/TP-510-42623, Jan. 2008, 14 pages, NREL, USA.

Weiss, N. D., et al., "Impact of corn stover composition on hemicellular conversion during dilute acid pretreatment and enzymatic cellulose digestibility of the pretreated solids", *Bioresource Technology*, 2010, vol. 101, pp. 674-678, Elsevier Ltd.

Zhu, L., et al., "Multiple linear regression model for predicting biomass digestibility from structural features", *Bioresource Technology*, 2010, vol. 101, Elsevier Ltd.

\* cited by examiner

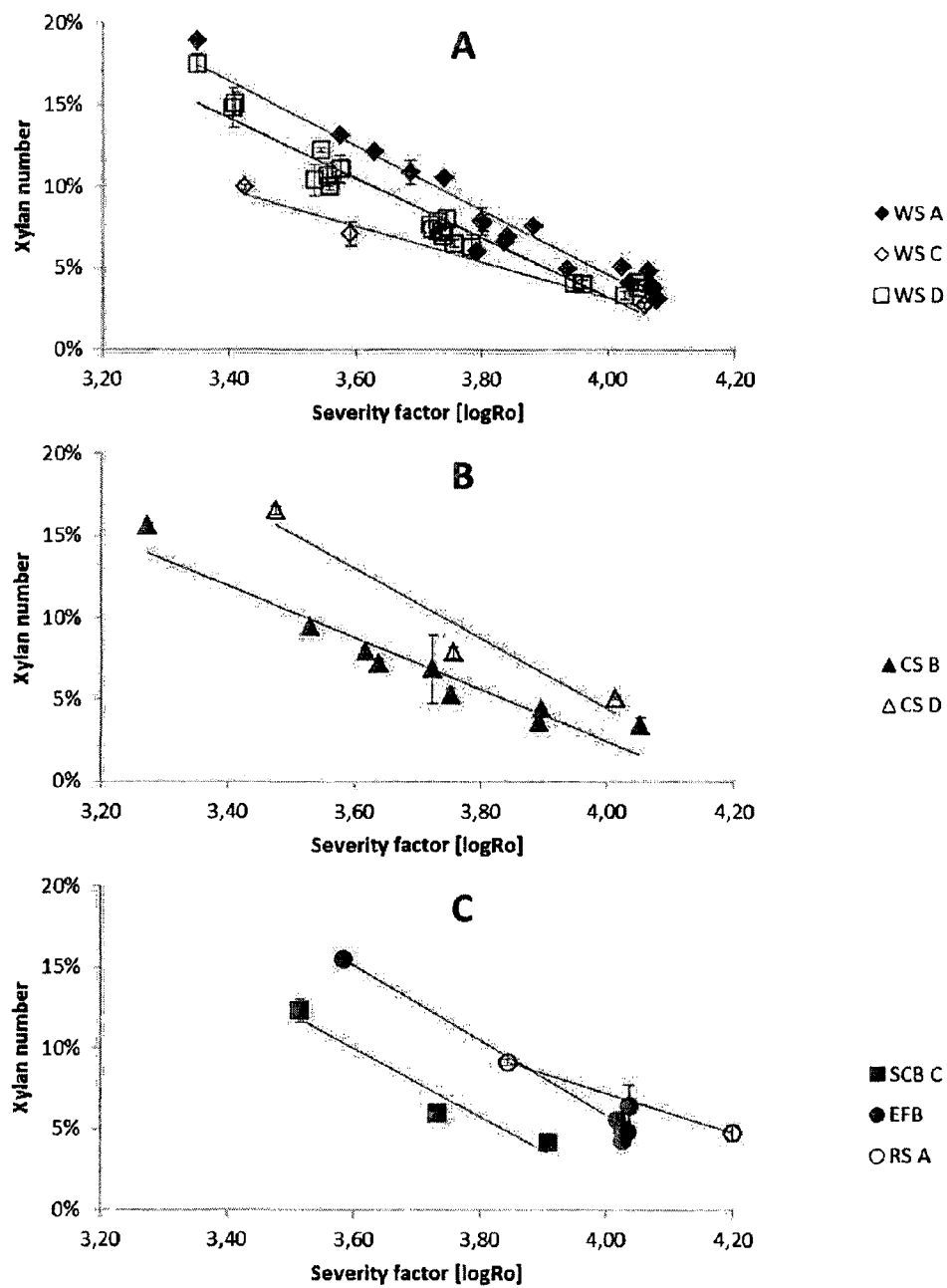
Figure 1. Xylan number as a function of severity factor for a) Three different harvest years of wheat straw (WS A, C and D) from Denmark, b) Two different batches of dried corn stover (CS B and D) from USA and c) Sugar cane bagasse (SCB) and empty fruit bunches (EFB) from Malaysia and rape straw (RS) from Denmark.

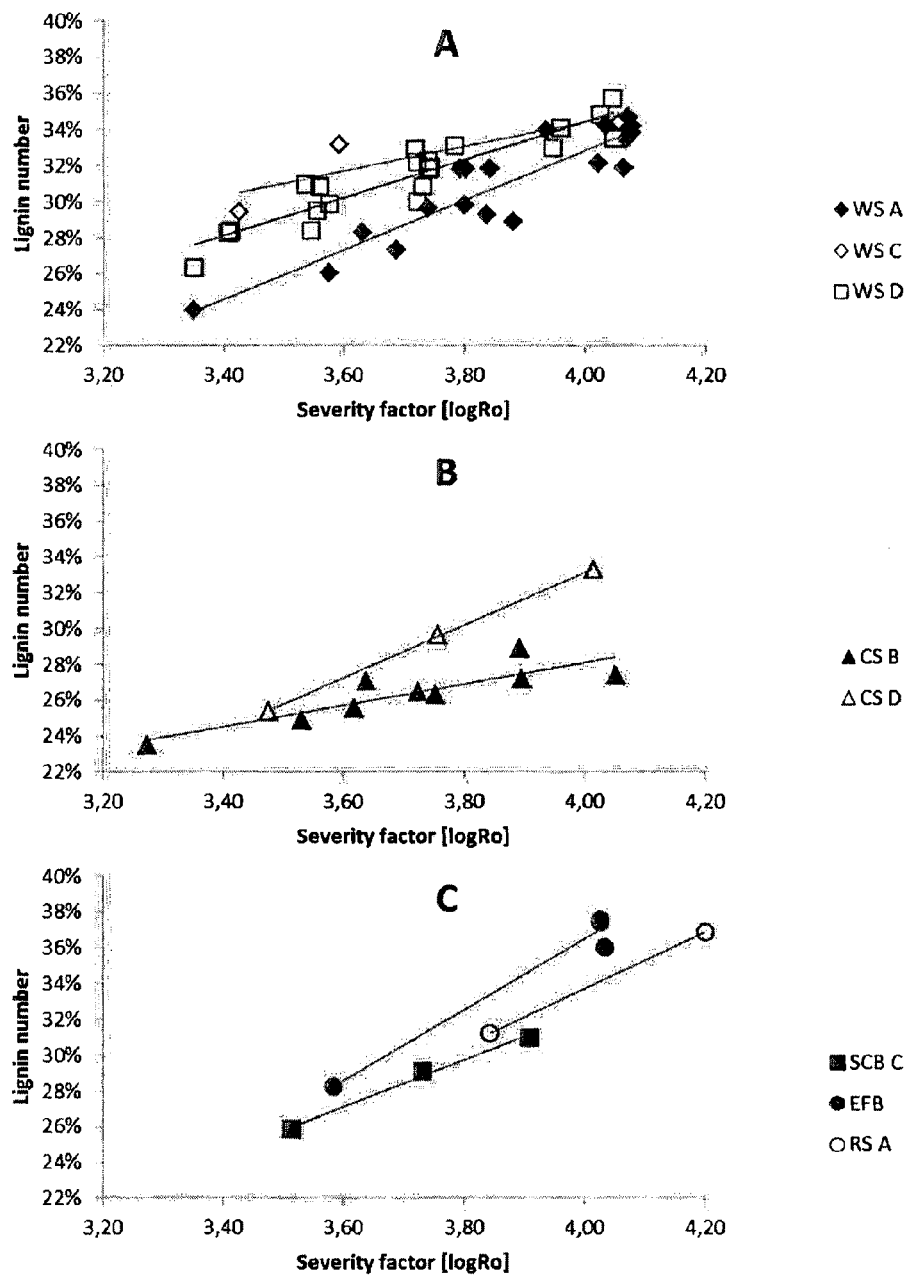
Figure 2: Lignin number as a function of severity factor for a) Three different harvest years of wheat straw (WS A, C and D) from Denmark, b) Two different batches of dried corn stover (CS B and D) from USA and c) Sugar cane bagasse (SCB) and empty fruit bunches (EFB) from Malaysia and rape straw (RS) from Denmark.

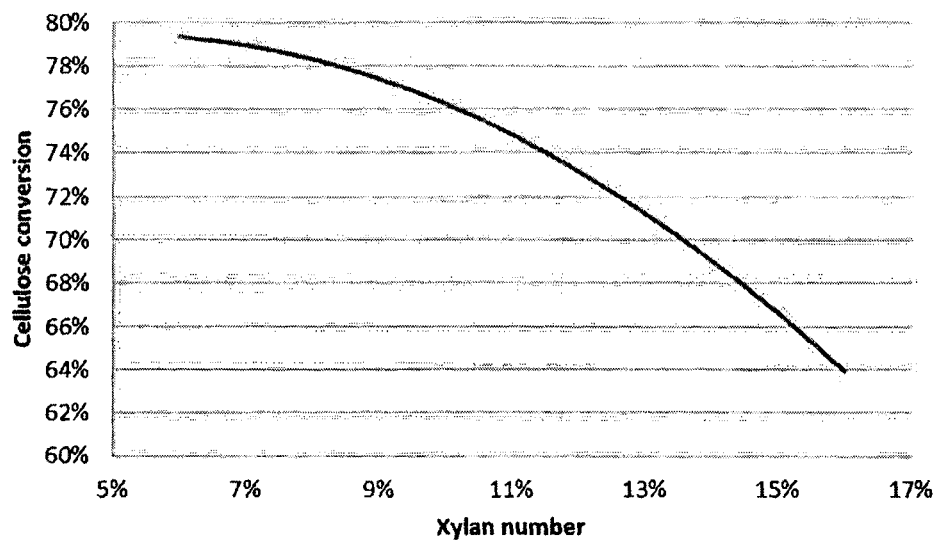
Figure 3: Conversion of glucan as a function of xylan number for pretreated wheat straw.
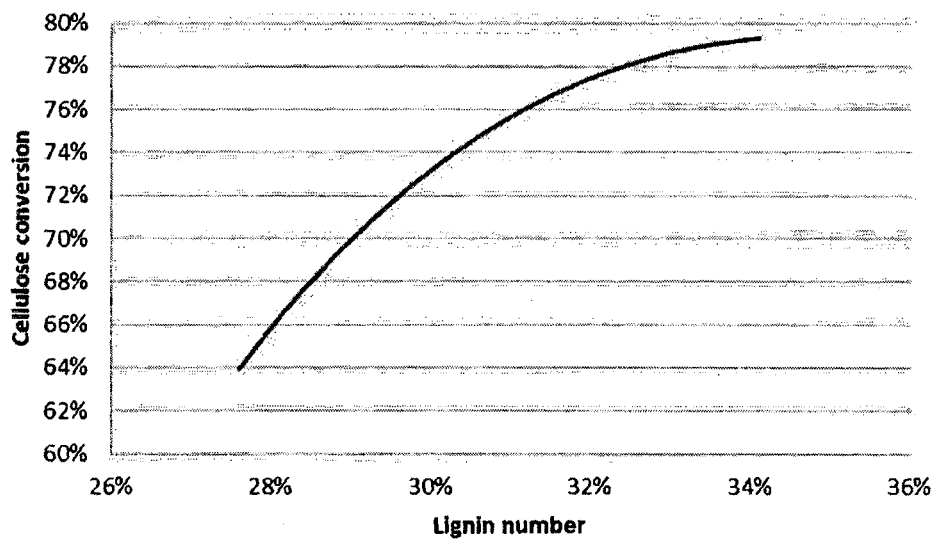
Figure 4. Conversion of glucan as a function of lignin number for pretreated wheat straw.

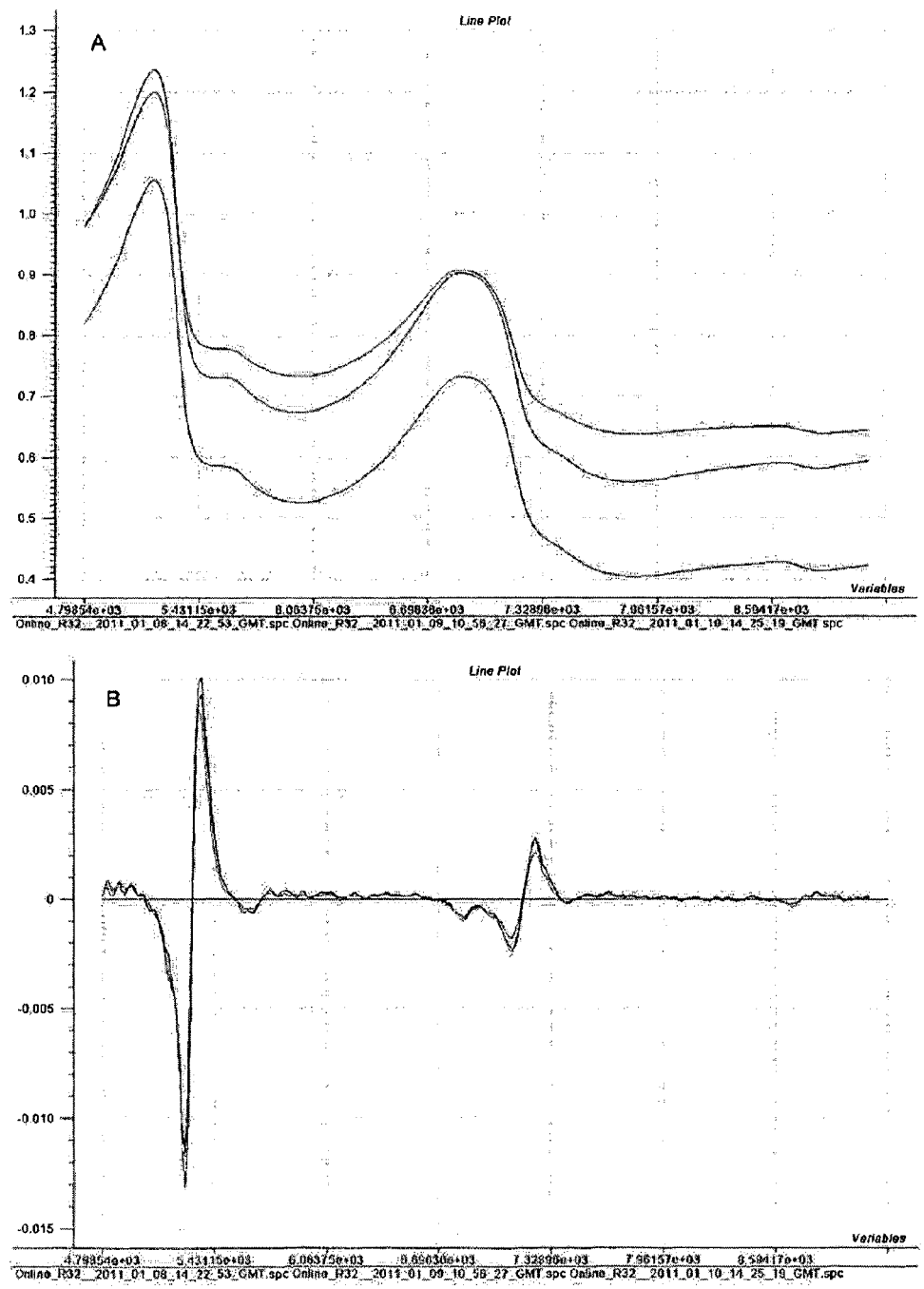
Figure 5. Representative examples of NIR spectra (A) Raw spectra, (B) Savitzky-Golay second derivative pretreated spectra.

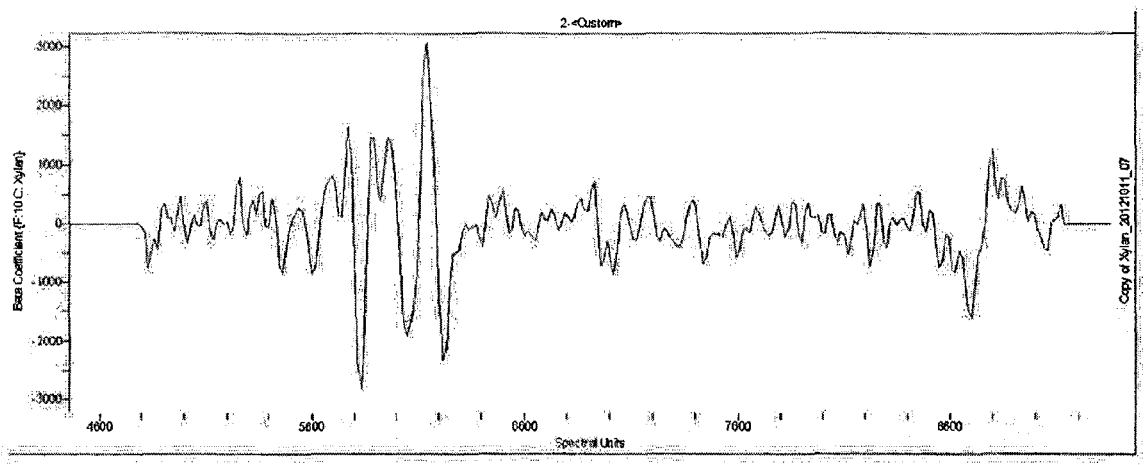
Figure 6. Regression coefficients for xylan number NIR spectral model.

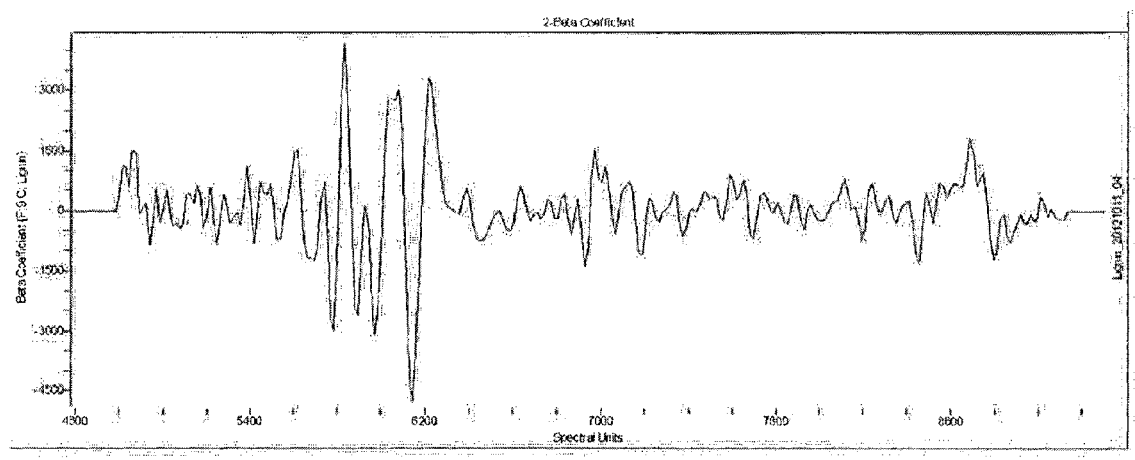
Figure 7. Regression coefficients for lignin number NIR spectral model.

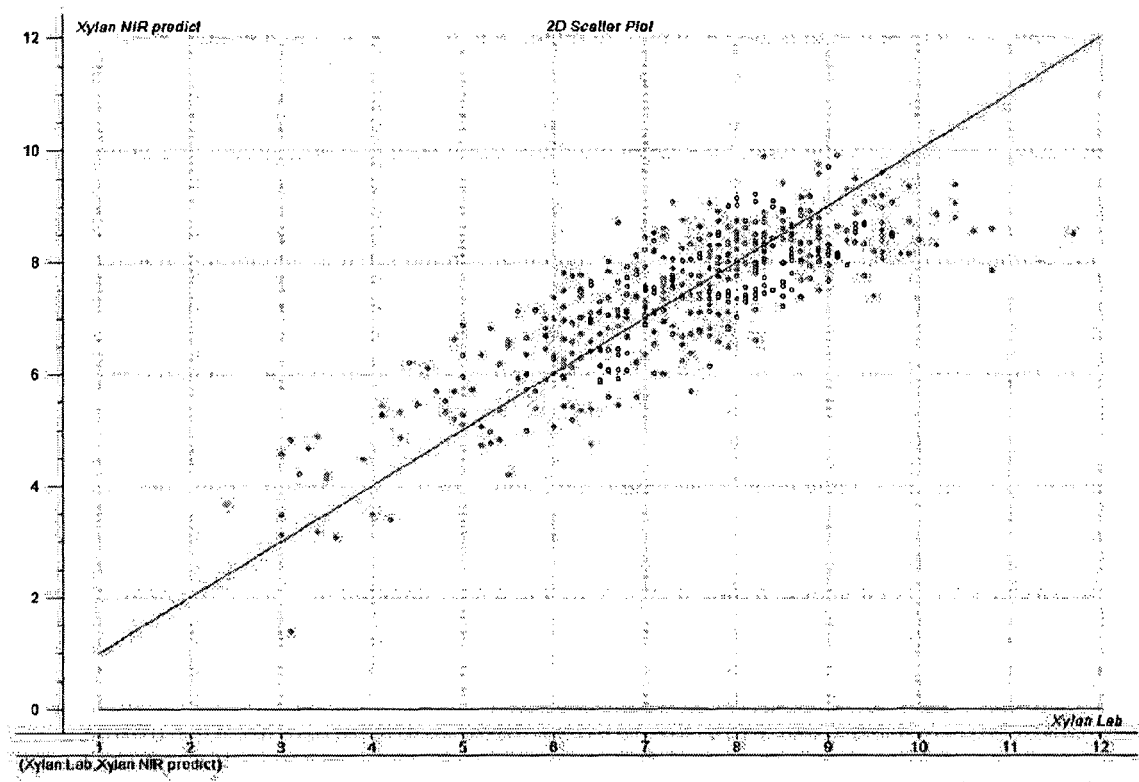
Figure 8. Predicted versus measured cross validation for online NIR measurement of xylan number.

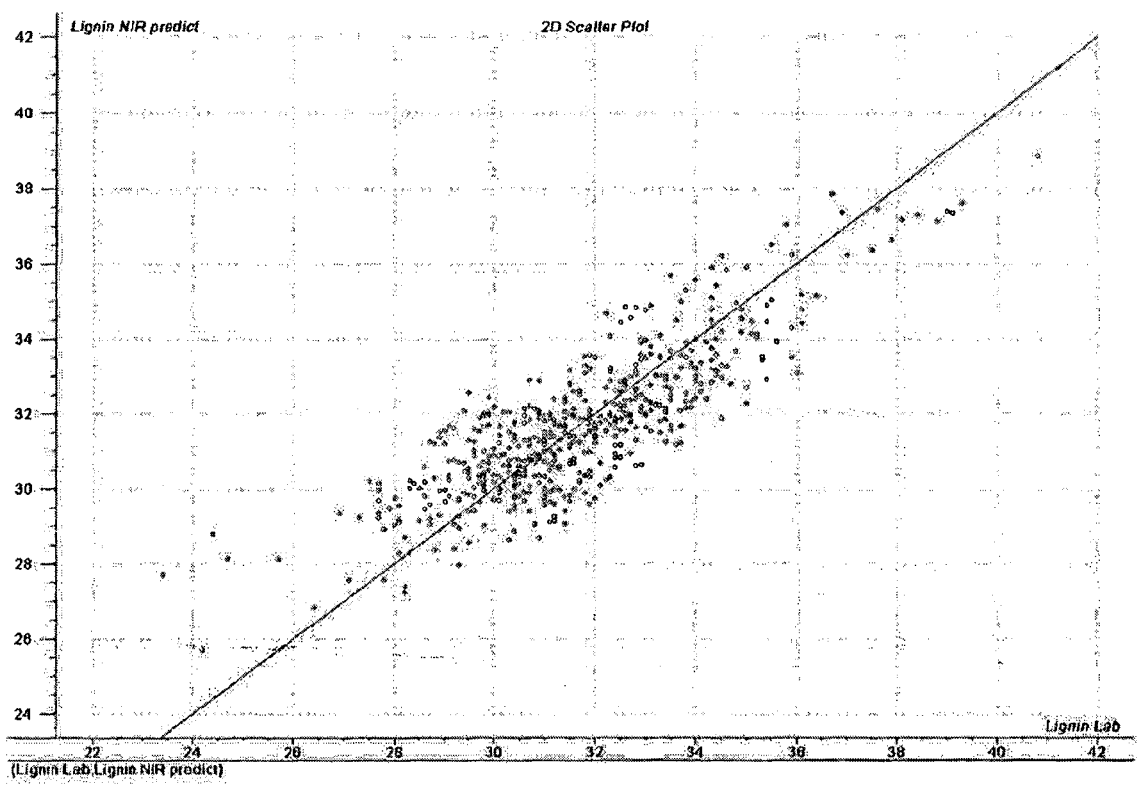
Figure 9. Predicted versus measured cross validation for online NIR measurement of lignin number.

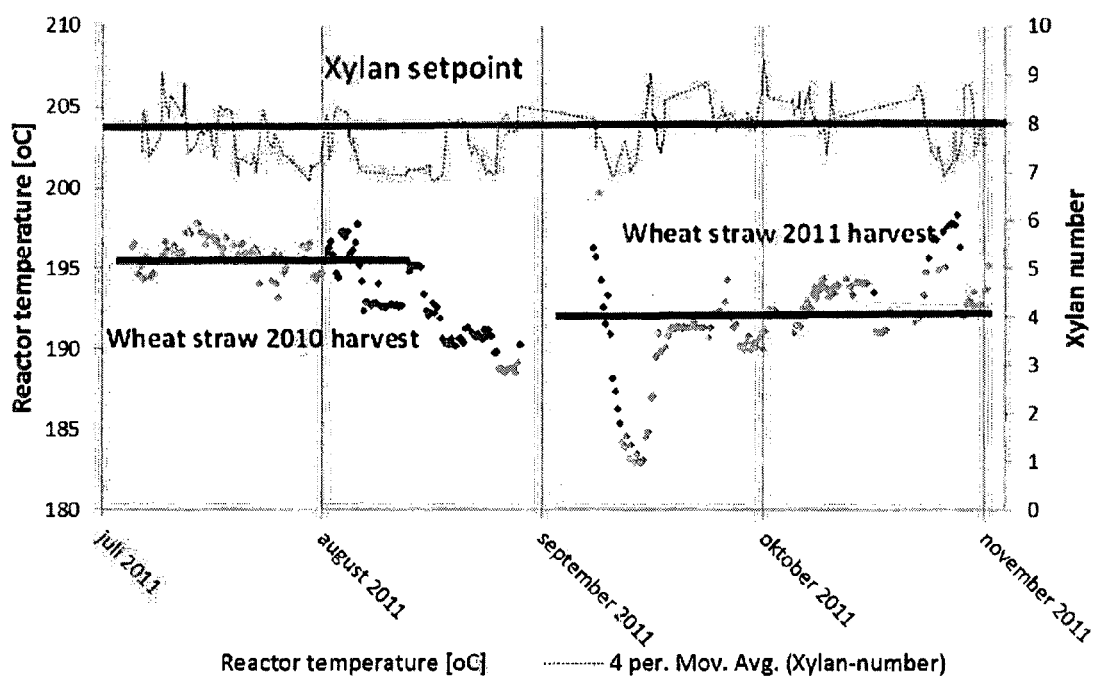
Figure 10. Feedback control of the pretreatment reactor at Kalundborg demonstration plant.

METHOD OF PROCESSING LIGNOCELLULOSIC BIOMASS USING FEEDBACK CONTROL OF HYDROTHERMAL PRETREATMENT

FIELD

The invention relates in general to methods of processing lignocellulosic biomass using hydrothermal pretreatment and in particular to methods where pretreatment is controlled by feedback monitoring of a defined pretreatment "end point" measured in the pretreated biomass output stream.

Great interest has arisen in so-called "second generation" biorefining, in which useful fermentation products are obtained from lignocellulosic biomass such as crop wastes (stalks, cobs, pits, stems, shells, husks, etc. . . . ), grasses, straws, wood chips, waste paper and the like. In "second generation" technology, fermentable 6-carbon and 5-carbon sugars are liberated from biomass polysaccharide polymer chains by enzymatic hydrolysis or, in some cases, by pure chemical hydrolysis. The fermentable sugars obtained from biomass conversion in a "second generation" biorefinery can be used to produce fuel ethanol or, alternatively, other fuels such as butanol, or lactic acid monomers for use in synthesis of bioplastics, or many other products.

Because of limitations of its physical structure, lignocellulosic biomass cannot be effectively converted to fermentable sugars by enzymatic hydrolysis without some pretreatment process. A wide variety of different pretreatment schemes have been reported. From an environmental and "renewability" perspective, hydrothermal pretreatments are especially attractive. These utilize pressurized steam/liquid hot water at temperatures on the order of 160-230° C. to gently melt hydrophobic lignin that is intricately associated with hemicellulose and cellulose strands, to solubilize a major component of hemicellulose, rich in 5 carbon sugars, and to disrupt cellulose strands so as to improve accessibility to productive enzyme binding. Hydrothermal pretreatments can be conveniently integrated with existing coal- and biomass-fired electrical power generation, plants to efficiently utilize turbine steam and "excess" power production capacity.

The "severity" of hydrothermal pretreatment refers to the harshness of conditions to which biomass feedstock has been subject. A variety of different composite parameters have been proposed that provide a scalar index by which different pretreatments schemes may be compared. Classic "severity, " Ro, is defined as (residence time in minutes)×(EXP[(pretreatment temperature−100)/14.75]) and is typically referred to as a logarithmic value, log Ro. Many hydrothermal pretreatment schemes such as dilute acid pretreatment and acidic steam explosion require relatively strong acid conditions but can typically be practiced at lower temperatures. Thus, a second severity parameter, Ro', is often used which includes a pH dimension such that, expressed as a log value, log Ro' is simply log Ro−pH. Some hydrothermal and other pretreatment schemes depend on relatively high pH conditions, such as ammonia fiber explosion and alkaline wet oxidation. Accordingly, still another severity parameter, Ro", is reported which accounts for the pH dimension such that log Ro" is log Ro+pH.

In the case of hydrothermal pretreatments, it is well known in the art, and has been widely discussed, that pretreatment severity must be optimized between conflicting tendencies. Severity should be sufficiently high so as to open lignocellulose structure for productive enzyme binding and thereby achieve reasonable conversion yields from the enzymatic hydrolysis reaction. Yet severity should also be sufficiently low so as to minimize loss of C5 sugars from hemicellulose and the associated increased production of byproducts of the pretreatment reaction that can inhibit fermentive organisms.

In production scale processing of lignocellulosic biomass, the ultimate effectiveness of hydrothermal pretreatment at fixed severity, as measured by enzymatic digestibility (conversion of polysaccharides to monomer sugars), is surprisingly variable. Even biomass feedstocks from a single species, obtained from a single growing region, can vary considerably in relative composition of hemicellulose, ash, lignin and cellulose. Thus, similar feedstocks that are pretreated to a fixed severity can, nevertheless, produce variable end results in enzymatic hydrolysis. See e.g. (Lindedam et al. 2010; Liu et al. 2010; Weiss et al. 2010).

Other groups have suggested previously that more consistent hydrolysis results can be obtained in production scale processing through feedback control of pretreatment systems based on online monitoring of some characteristic of pretreated material that serves as an indicator of the material having reached a defined pretreatment "end point." See e.g. (Weiss et al. 2010). However the question of which "endpoint" measure to use remains controversial, with many conflicting results having been reported.

Depending on the biomass feedstock used and the manner of its pretreatment, a variety of different measurements have been reported that can be used as a pretreatment "end point" measure. Absence of lignin content, acetyl content or cellulose crystallinity measured in water insoluble solids have been reported as providing the best predictors of enzymatic digestibility with rice straw and with wood chips pretreated by ammonia fiber explosion. See e.g. (Gollapalli et al. 2002; Zhu e al. 2010; Chandra et al. 2007). Measurements of residual xylan content in insoluble solids following pretreatment have been reported to predict enzymatic digestibility in wheat straw (Kabel et al. 2007; Perez et al. 2007) that was hydrothermally pretreated in the pH range 2-7. With other feedstocks, subject to other pretreatments, residual xylan content in insoluble solids has not consistently proved useful as a predictor of digestibility. In dilute acid pretreated corn stover, residual xylan content has variously been reported to predict (Bura et al. 2009; Jeoh et al. 2007) and not to predict (Weiss et al. 2010) enzymatic digestibility.

In cases where residual xylan content in insoluble solids of pretreated biomass could be used to predict digestibility, both in wheat straw (Kabel et al. 2007) and in corn stover (Jeoh et al. 2007), predictive power could only be sustained above a lower threshold of pretreatment severity. Digestibility was shown to be unstable at residual xylan levels higher than 7% in wheat straw (Kabel et al. 2007). No correlation of residual xylan content with digestibility could be seen at residual xylan levels higher than 7.5% in corn stover (Jeoh et al. 2007).

The prior art teaches that residual xylan measurement cannot, itself, provide an accurate predictor of digestibility at low severity levels corresponding to residual xylan higher than 7.5%. However, we have discovered that a composite measure which combines measurements of both residual xylan content in insoluble solids and also of soluble xylose/xylo-oligomer concentration provides a reliable pretreatment "end point" measure. This composite measure, which we term "xylan number," can be easily determined online and provides an accurate predictor of digestibility at low severity for hydrothermally pretreated biomass.

Alternatively, a composite "end point" measure can be used which combines measurements of both lignin content in insoluble solids and also of a variety of unhydrolysed solids including condensation and polymerization products arising from hemicellulose degradation during pretreatment. This composite measure, which we term "lignin number," can also be easily determined online and similarly provides an accurate predictor of digestibility at low severity for hydrothermally pretreated biomass.

Using feedback control of pretreatment, based on either of these composite "end point" measures, reactor conditions can be rapidly adjusted to accommodate variability of incoming feedstocks in production scale, minimizing the incidence of pretreatment inefficiencies.

BRIEF DESCRIPTION OF THE FIGURES

FIG. 1 shows dependence of xylan number on pretreatment severity log(Ro) for (A) three different harvest years of wheat straw from Denmark, (B) two different sources of dried corn stover, (C) sugar can bagasse and empty fruit bunches from Malysia and rape straw from Denmark.

FIG. 2 shows dependence of lignin number on pretreatment severity log(Ro) for (A) three different harvest years of wheat straw from Denmark, (B) two different sources of dried corn stover, (C) sugar can bagasse and empty fruit bunches from Malysia and rape straw from Denmark.

FIG. 3 shows conversion of glucan as a function of xylan number for pretreated wheat straw.

FIG. 4 shows conversion of glucan as a function of lignin number for pretreated wheat straw.

FIG. 5 shows representative examples of NIR spectra of pretreated biomass output stream (A) raw spectra and (B) Savitzky-Golay second derivative spectra.

FIG. 6 shows regression coefficients for xylan number NIR spectral model.

FIG. 7 shows regression coefficients for lignin number NIR spectral model.

FIG. 8 shows predicted versus measured cross validation for online NIR measurement of xylan number.

FIG. 9 shows predicted versus measured cross validation for online NIR measurement of lignin number.

FIG. 10 shows feedback control of the pretreatment reactor at Kalundborg demonstration plant in response to xylan number measurements in the pretreated biomass output stream.

DETAILED DESCRIPTION OF EMBODIMENTS

In some embodiments, the invention provides a method of processing lignocellulosic biomass comprising
providing lignocellulosic biomass feedstock,
pretreating said biomass feedstock by continuous hydrothermal pretreatment in a pressurized reactor,
measuring xylan number in the output stream of pretreated biomass from the pretreatment reactor, and
controlling the pretreatment reactor so as to maintain, in the output stream of pretreated biomass, a pre-determined level of measured xylan number.

In some embodiments, the invention provides a method of processing lignocellulosic biomass comprising
providing lignocellulosic biomass feedstock,
pretreating said biomass feedstock by continuous hydrothermal pretreatment in a pressurized reactor,
measuring lignin number in the output stream of pretreated biomass from the pretreatment reactor, and
controlling the pretreatment reactor so as to maintain, in the output stream of pretreated biomass, a pre-determined level of measured lignin number.

"Lignocellulosic biomass" refers to any type of plant biomass.

Any suitable lignocellulosic biomass may be used, including soft lignocellulosic biomasses such as at least wheat straw, corn stover, corn cobs, empty fruit bunches, rice straw, oat straw, barley straw, canola straw, sorghum, sweet sorghum, soybean stover, rye grass, switch grass, Bermuda grass and other grasses, bagasse, beet pulp, corn fiber, or any combinations thereof. Hard lignocellulosic biomass may also be used including at least hardwood, softwood, wood pulp, and forestry wastes. Lignocellulosic biomass may comprise other lignocellulosic materials such as paper, newsprint, cardboard, or other municipal or office wastes. Lignocellulosic biomass may be used as a mixture of materials originating from different feedstocks, may be fresh, partially dried, fully dried or any combination thereof.

Suitable lignocellulosic biomass typically comprises cellulose in amounts between 20 and 50% of dry mass prior to pretreatment, lignin in amounts between 10 and 40% of dry mass prior to pretreatment, and hemicellulose in amounts between 5 and 40%.

Lignocellulosic biomass comprises crystalline cellulose fibrils intercalated within a loosely organized matrix of hemicellulose and sealed within an environment rich in hydrophobic lignin. While cellulose itself comprises long, straight chain polymers of D-glucose, hemicellulose is a heterogeneous mixture of short, branched-chain carbohydrates including monomers of all the 5-carbon aldopentoses (C5 sugars) as well as some 6-carbon (C6) sugars including glucose and mannose. Lignin is a highly heterogeneous polymer, lacking any particular primary structure, and comprising hydrophobic phenylpropanoid monomers.

Enzymatic hydrolysis of lignocellulosic biomass using cellulase and hemicellulase enzymes is not particularly effective in the absence of some treatment, which is typically termed "pretreatment." Pretreatment reduces the barrier to productive cellulase enzyme binding which is created by the intimate integration of cellulose within lignin and hemicellulose environments. Pretreatment further disrupts the crystalline structure of cellulose chains, which are generally resistant to enzymatic hydrolysis.

A wide variety of different pretreatment technologies are known in the art. For a recent review, see (Alvira 2010). The claims herein relate to methods of processing lignocellulosic biomass wherein the biomass feedstock is subject to hydrothermal pretreatment.

"Hydrothermal pretreatment" refers to the use of water, either as hot liquid, vapour steam or pressurized steam comprising high temperature liquid or steam or both, to "cook" biomass, at temperatures of 120° C. or higher, either with or without addition of acids or other chemicals. In some embodiments, hydrothermal pretreatment is conducted without supplemental oxygen as required for wet oxidation pretreatments, or without addition of organic solvent as required for organosolv pretreatment, or without use of microwave heating as required for microwave pretreatments. In some embodiments, hydrothermal pretreatment is conducted at temperatures of 140° C. or higher, or at 150° C. or higher, or at 160° C. or higher. The pH at which biomass is hydrothermally pretreated refers to the pH of a wetted biomass/biomass slurry as it enters a pretreatment reactor. The total solids content at which biomass is hydrothermally pretreated refers to the combined w/w percentage of water insoluble and water soluble solids present in the wetted biomass/biomass slurry as it enters a pretreatment reactor.

Hydrothermal pretreatments may be conducted at different degrees of wetting, i.e., at different dry matter (DM) content. The raw biomass feedstock comprises some quantity of water as well as a "dry weight" that remains after all water is removed. "Dry matter" (DM) as used herein refers to solids including both water insoluble solids and water soluble solids. % DM refers to weight %. For example, biomass feedstocks pretreated at 18% DM (i.e., loaded into the pretreatment reactor at 18% total solids) typically exist as wetted fiber, while biomass feedstocks pretreated at 10% DM or lower typically exist as a liquid slurry. The greater the extent to which feedstocks have been subject to particle size reduction by chopping, milling or other processes, the greater will be the tendency to form liquid slurry at any given DM level.

The total solids content of hydrothermally pretreated biomass comprises both a liquid component (hereafter "liquid fraction") and a water insoluble "solid" component. The "solid" component comprises insoluble solids. However, as isolated from liquid fraction, in the absence of washing or other steps, the "solid" component is swelled with "liquid fraction." The "liquid fraction" comprises solubilized hemicellulose, comprising predominantly C5 sugars with some C6 sugars, as well as byproducts of the pretreatment reaction.

Hydrothermal pretreatment may be conducted by a variety of methods well known in the art. Steam pretreatment typically may be conducted either as a "steam explosion" or using high pressure steam without explosive release of pretreated biomass. Steam pretreatment is typically conducted at high temperatures, between 170 and 220° C., and at high pressures, between 4 and 20 bar, where water exists as a mixture of liquid and vapour. In some embodiments, lignocellulosic biomass is pretreated by hydrothermal pretreatment at temperatures between 170 and 200° C. In some embodiments, biomass feedstocks may be subject to particle size reduction and/or other mechanical processing such as grinding, milling, shredding, cutting or other processes prior to hydrothermal pretreatment. In some embodiments, biomass feedstocks may be washed and/or leached of valuable salts prior to pretreatment, as described in (Knudsen et al. 1998).

Hydrothermal pretreatment is continuous where a flow of biomass into and out of a pressurized pretreatment reactor is maintained continuously, except for temporary stops.

A variety of different methods may be used for removing preteated biomass from a hydrothermal pretreatment reactor. In some embodiments, biomass is removed from the reactor by explosive release or "steam explosion," whereby biomass is suddenly transferred from reactor pressure of >4 bar or between 4 and 20 bar to atmospheric pressures. Steam explosion typically destroys the fibrous structure of the biomass, leaving a pretreated biomass having both "liquid fraction" and water insoluble "solid" component combined in a thick paste. In some embodiments, pretreated biomass is released non-explosively, for example, by means of a sluice device, such as the "particle pump" described in U.S. Ser. No. 13/043,486. Using a "particle pump" to remove biomass from the pretreatment reactor also provides both the "liquid fraction" component and also the water insoluble "solid" component of the pretreated biomass in a combined mixture.

In some embodiments, biomass can be released non-explosively into a hydrocyclone device or "cold discharger," which can be filled with water or recycled process fluids. Hydrocyclone devices, such as those described in WO 2009/147512, may be filled with fresh water or with relatively dilute solutions (typically <10 g/kg dissolved solids, or <20 g/kg, or <50 g/kg, or <100 g/kg) obtained as condensate from evaporative or other biorefinery processes.

During hydrothermal pretreatment, solubilization of hemicellulose is associated with changes in the distribution of xylan between solid and liquid phases. As used herein the term "xylan" is used generically to refer to all oligo- and polysaccharide polymers of xylose, which is the predominant C5 sugar comprising hemicellulose. Pretreatment is inevitably associated with some loss of xylan content as a consequence of its conversion to chemical byproducts. However, as a general rule, as pretreatment increases in severity, a greater proportion of xylan content is lost from the insoluble solid component while a greater proportion of xylan content is gained in the liquid fraction. This relationship holds across all levels of severity that result in levels of xylan content in the insoluble solid component of about 16% or less as a percentage of dry matter.

It is universally accepted that optimal conversion yields depend on pretreatment providing both an "opening" of the lignocellulosic matrix and also on a disruption of cellulose strand structure. Hydrothermal pretreatments conducted at extreme alkaline pH achieve such complete lignin removal that lignocellulosic matrix is "opened" to productive enzyme binding, despite substantial residual xylan content in the water insoluble "solid" component. Hydrothermal pretreatments conducted at extreme acidic pH achieve more complete solubilization of hemicellulose at any given temperature, and can thus typically "open" lignocellulose matrix to efficient enzymatic hydrolysis with comparatively lower temperatures and residence times. Hydrothermal pretreatments conducted in the pH range 2.5 to 8 are typically termed "autohydrolysis" treatments, since these do not rely on added acid or base catalyst. Autohydrolysis requires somewhat higher temperatures, but avoids requirement for added industrial chemicals. In some embodiments, hydrothermal pretreatment is conducted using autohydrolysis.

The "liquid fraction" obtained after pretreatment refers to the liquid phase of pretreated biomass, comprising added water/steam, as it exists immediately after pretreatment and optionally after equilibration to 25° C. and atmospheric pressure. It will be readily understood that "liquid fraction" exists whether or not any physical solid/liquid separation step is used. Liquid fraction comprises primarily water and water soluble material.

The "fiber fraction" obtained after pretreatment refers to the insoluble solid phase component of pretreated material in the absence of "liquid fraction." It will be readily understood that "liquid fraction" and "fiber fraction" exist whether or not any physical solid/liquid separation step is used. The solids content of the "fiber fraction" comprises primarily lignin and unhydrolysed cellulose and hemicellulose. The term "solid fraction" is used to refer to water insoluble solids in which some "liquid fraction" remains, for example, in material obtained after a solid/liquid separation step that has been only partially washed so that for example approximately 30-15% of the total dissolved solids after pretreatment remain in the "fiber fraction."

As used herein, the terms "high severity" or "low severity" used in reference to hydrothermal pretreatments at pH<8 that do not rely on a separate hemicellulose separation step refers to the residual xylan content in the water insoluble "fiber fraction" component of pretreated biomass. "High severity" pretreatment produces pretreated biomass in which residual xylan content in the water insoluble "fiber fraction" is between 0 and 5% as a percentage of dry matter. "Low severity" pretreatment produces pretreated biomass in which residual xylan content in the water insoluble "fiber fraction" is between 7.5 and 8%. "Lower severity" pretreatment produces pretreated biomass in which residual xylan content in the water insoluble "fiber fraction" is between 8 and 9%. "Very low severity" pretreatment produces pretreated biomass in which residual xylan content in the water insoluble "fiber fraction" is between 9 and 16%.

Hydrothermal pretreatments conducted at pH<8 do not, themselves, achieve complete lignin removal from pretreated biomass. The lignocellulosic matrix of biomass pretreated under these conditions includes both substantial lignin and xylan content. Xylan content in the water insoluble solid "fiber fraction" component of such pretreated biomass is detrimental to enzymatic hydrolysis. Xylan on the fiber surface hinders productive cellulase binding. See (Kabel et al. 2007; Jeoh et al 2007). Xylan content in the water insoluble solid "fiber fraction" component of biomass pretreated at pH>8 is typically higher than levels achieved at pH<8.

Residual xylan content in the water insoluble solid "fiber fraction" component is typically quite low in pretreatment schemes that rely on multiple-stage pretreatments, such as those described in WO2011/043935, WO1009/108733, and WO2010/113129, where an initial pretreatment stage achieves nearly complete hemicellulose solubilization. In some embodiments, pretreatment is conducted using single-stage pretreatment or in some other manner than by multiple-stage pretreatment.

Where biomass is hydrothermally pretreated at pH<8 to high severity, residual xylan content in the water insoluble solid "fiber fraction" component provides a simple and convenient assessment of pretreatment degree that is alternative to Ro and Ro' and that provides an equally effective pretreatment "end point," that is, an equally effective predictor of enzymatic digestibility on the basis of which process conditions may be optimized. (Kabel et al. 2007)

However, where biomass is hydrothermally pretreated at pH<8 to low severity, residual xylan content has not previously been considered useful as a predictor of enzymatic digestibility or as a pretreatment "end point" measure. It has previously been reported that residual xylan content in the water insoluble "fiber fraction"ceases to be, itself, sufficiently predictive of enzymatic digestibility at low severity. (Jeoh et al., 2007; Kabel et al., 2007). Using more recent generations of commercially available cellulase preparations optimized for lignocellulosic biomass conversion, we have discovered that residual xylan content is less obstructive of enzymatic hydrolysis than with previous generations of cellulase preparation. We have discovered that a reliable pretreatment "end point" can be determined, even at low severity, lower severity, and very low severity, which combines information about residual xylan content in the water insoluble"fiber fraction"with information about soluble xylan in the liquid fraction. We term this measurement "xylan number."

"Xylan number" refers to a measurement of total xylan content, expressed as weight percentage of dry matter, which measurement includes a measurement of residual xylan in the insoluble "fiber fraction"and also some contribution of xylan from liquid fraction, such that at least 0.8% dissolved solids in absolute terms are included in the measurement.

In measuring xylan number, the contribution from xylan content of liquid fraction depends on the manner in which samples are prepared for measurement. In some embodiments, xylan number can be measured in whole slurry (i.e., pretreated biomass without solid/liquid separation). Pretreatment of a biomass feedstock will typically result in some dilution from added water content associated with hydrothermal pretreatment, for example, low severity pretreatment of biomass at 35% DM will typically produce a pretreated biomass slurry having about 22% DM, of which about 6% in absolute terms comprises dissolved solids. A substantial component of these dissolved solids typically comprise xylan—on the order of 40-60%.

In some embodiments, a solid/liquid separation step may be applied to the pretreated biomass to produce a solid fraction for measurements of xylan number. For biomass pretreated to low, lower or very low severity, solid fraction produced using solid/liquid separation techniques typically used in production scale processing typically has between 30-50% DM content. Of this DM content, typically between 3.7 to 2.6% in absolute terms comprises dissolved solids. For example, solid/liquid separation may be achieved using a relatively inexpensive screw press, which can typically achieve DM content of the solid fraction to levels up to 45%. Alternatively a twin roll press or a twin wire press may be used, which can typically achieve DM of the solid fraction to levels in the range 30-45%. In some embodiments a belt press, drum filter, centrifuge or decanter centrifuge may be used.

In some embodiments, solid fraction may be washed by any suitable means known in the art to further remove dissolved solids prior to measurement of xylan number. For example, a solid fraction from biomass pretreated to very low severity, initially pressed to 30% dry matter and washed with 3.0 kg water/kg DM will typically comprise about 2% dissolved solids in absolute terms (that is about 2 of the 30% DM comprises dissolved solids). The same solid fraction washed with only 1.5 kg water/kg DM will typically comprise about 5% dissolved solids in absolute terms. The same solid fraction unwashed will typically comprise about 8% dissolved solids in absolute terms.

In these examples, if the xylan number of the solid fraction pressed to 30% DM and washed with 3.0 kg water/kg DM was 10 wt. %, then the measured xylan number for the same solid fraction washed with only 1.5 kg water/kg DM would be about 11.4 wt. %, the same solid fraction unwashed would have a xylan number of about 14.2 wt. %, and whole slurry from the same pretreated biomass would have a xylan number of about 17.7.

Xylan number provides a relatively linear correlation with pretreatment severity log Ro, even at very low severity, where the measurement includes a contribution from at least 0.8% dissolved solids, in absolute terms (that is, 0.8 of the total dry matter % comprises dissolved solids). In some embodiments, xylan number is measured in samples comprising at least 0.8% dissolved solids in absolute terms, or at least 1%, or at least 2%, or more than 0.8% but less than 9%, or more than 0.8% but less than 7%, or more than 0.8% but less than 6%, or more than 0.8% but less than 5%, or more than 0.8% but less than 4%, or more than 0.8% but less than 3%, or more than 0.8% but less than 2%.

It will be readily understood by one skilled in the art that the absolute magnitude of xylan number will differ depending on the scheme used for sampling pretreated biomass in order to determine xylan number, with or without solid/liquid separation, and with or without washing of solid fraction. However, where a consistent sample scheme is used, the resulting xylan number values can readily be correlated to pretreatment severity and, accordingly, can be used as an "end point" measure for feedback control of the pretreatment reactor.

In some embodiments, pretreated biomass is subject to solid/liquid separation to provide a solid fraction at 25-50% total solids which is swelled with liquid fraction obtained after pretreatment. This solid fraction is then partially washed by mixing with water in the ratio of total solids to water of 1:3. The solid fraction washed in this manner is then pressed to 25-50% total solids where approximately 15-30% of the dissolved solids are left in the solid fraction. Xylan content of the solid fraction washed in this manner as determined using the method of A. Sluiter, et al., "Determination of structural carbohydrates and lignin in biomass," US National Renewal Energy Laboratory (NREL) Laboratory Analytical Procedure (LAP) with issue date Apr. 25, 2008, as described in Technical Report NREL/TP-510-42618, revised April 2008, which is expressly incorporated by reference herein in entirety. In some embodiments, carbohydrate determinations are made using a Rezex column from Dionex.

In some embodiments, biomass feedstocks are pretreated to severity log Ro between 3.2 and 4.2, or between 3.5 and 3.9. In some embodiments, biomass feedstocks are pretreated to severity corresponding to xylan number as measured in a 30% DM solid fraction partially washed by mixing with water in the ratio of total solids to water of 1:3 of between 7 and 14, or between 7.5 and 14, or between 7.6 and 14, or between 7.7 and 14, or between 7.8 and 14, or between 7.9 and 14, or between 8 and 14, or between 8 and 12, or between 9 and 11.

Total xylan measurements used to determine xylan number can be determined using a variety of methods well known in the art. In some embodiments, total xylan can be determined from direct chemical measurements well known in the art applied to samples withdrawn from the pretreated biomass output stream. In some embodiments, xylan number can be determined online using near-infra-red (NIR) spectroscopy, as described by Flames et al. 2003 and by WO2009/059176, each of which references is hereby incorporated by reference in entirety. Typically, in order to conduct online NIR measurements, a calibration against some specific chemical measurement is required. In such embodiments, complex NIR absorption spectra (800 nm to 2500 nm) of pretreated biomass are determined, along with specific chemical measurements of interest in the corresponding samples. The NIR spectra are then analysed by multivariate calibration techniques, such as partial least squares regression, to produce a NIR spectral model that "predicts" (measures) the chemical content of interest.

In order to determine calibration for NIR measurements, total xylan should ideally be determined using a method known in the art which determines both xylan content of insoluble solids and also xylan content of associated dissolved solids. One suitable chemical xylan measurement which can be used to determine calibration of an NIR spectral model for xylan number is the method of A. Sluiter, et al., "Determination of structural carbohydrates and lignin in biomass," US National Renewal Energy Laboratory (NREL) Laboratory Analytical Procedure (LAP) with issue date Apr. 25, 2008, as described in Technical Report NREL/TP-510-42618, revised April 2008.

In some embodiments, NIR spectra are determined online in the pretreated biomass output stream, in whole slurry, in solid fraction or in washed solid fraction using measurement techniques well known in the art. Xylan number is then determined by application to the measured complex NIR spectra of a NIR spectral model to predict xylan number determined by calibration against chemical measurements in references samples which determine both xylan content of insoluble solids and also xylan content of associated dissolved solids. In some embodiments, pH adjustment or other chemical additions may be introduced prior to NIR measurements. It will be readily understood by one skilled in the art that it can be advantageous to recalibrate a NIR spectral model where different biomass feedstocks are used, or where process conditions are changed.

As an alternative to "xylan number," another composite measurement which we term "lignin number" can be used as an "end point" measure for feedback control of pretreatment. "Lignin number" refers to a measure of "Klason lignin," which includes a measure of acid-insoluble residue, expressed as a weight percentage of dry matter, that comprises both total lignin content within insoluble solids and also a measurement of a variety of unhydrolysed solids including condensation and polymerization products arising from hemicellulose degradation during pretreatment.

"Lignin number" is a measure of material present in the measured sample which is insoluble in strong acid. The strength of acid used in to determine "lignin number" by chemical measurements can vary, provided the measurement includes a measurement of both lignin within insoluble solids and also of condensation and polymerization products arising from hemicellulose degradation during pretreatment. For example any suitable method for determination of so-called "Klason lignin" known in the art can be used for a chemical determination of "lignin number."

"Klason lignin" measurements used to determine lignin number can be determined using a variety of methods well known in the art. In some embodiments, Klason lignin can be determined from direct chemical measurements well known in the art applied to samples withdrawn from the pretreated biomass output stream. In some embodiments, lignin number can be determined online using near-infra-red (NIR) spectroscopy, as described previously herein for NIR measurements of xylan number.

In order to determine calibration for NIR measurements, Klason lignin should ideally be determined using a method known in the art which determines both lignin content of insoluble solids and also "pseudo lignin" content of insoluble solids and associated dissolved solids. One suitable Klason lignin measurement which can be used to determine calibration of an NIR spectral model for lignin number is the method of A. Sluiter, et al., "Determination of structural carbohydrates and lignin in biomass," US National Renewal Energy Laboratory (NREL) Laboratory Analytical Procedure (LAP) with issue date Apr. 25, 2008, as described in Technical Report NREL/TP-510-42618, revised April 2008.

In some embodiments, any of the methods described previously for preparing samples of pretreated biomass for determination of xylan number may be used for determination of lignin number. It will be readily understood by one skilled in the art that the absolute magnitude of lignin number will differ depending on the scheme used for sampling pretreated biomass in order to determine lignin number, with or without solid/liquid separation, and with or without washing of solid fraction. However, where a consistent sample scheme is used, the resulting lignin number values can readily be correlated to pretreatment severity and, accordingly, can be used as an "end point" measure for feedback control of the pretreatment reactor.

The xylan number or lignin number measured in the pretreated biomass output stream can be used as a pretreatment "end point" measure for feedback control of the pretreatment reactor. The continuous output of pretreated biomass is sampled and analysed, and the "end point" xylan number or lignin number measurement determined. The reactor conditions are then adjusted in an ongoing manner in response to the "end point" measure so as to maintain the "end point" measurement at a pre-determined level. In some embodiments, dwell time of biomass within the reactor can be adjusted in feedback response to the "end point" measurement, for example, by adjusting the rate at which biomass is moved through the continuous pretreatment system. In some embodiments, the steam pressure or water temperature applied to the continuous biomass pretreatment stream is adjusted or cooling water introduced in feedback response to the "end point" measurement. In some embodiments the sequence of "end point" measurement and corresponding adjustment of reactor conditions may be repeated over a regular interval, for example every minute, or every 5 minutes, or every hour. In some embodiments, reactor temperature can vary between about 170° C. and 200° C., and dwell time within the reactor can vary between about 4 minutes to 20 minutes, or between 10 to 20 minutes, or between 12 to 18 minutes.

One skilled in the art will readily imagine a variety of schemes for managing feedback control of hydrothermal pretreatment using measurements of xylan number or lignin number in the continuous output stream of pretreated biomass.

EXAMPLES

Example 1

"Xylan Number" Characterization of Solid Fraction as a Measure of Pretreatment Severity Wheat straw (WS), corn stover (CS), rape straw (RS), sweet sugarcane bagasse (SCB) and empty fruit bunches (EFB) were soaked with 0-10 g acetic acid/kg dry matter biomass, pH>4.0 and pH<8.0, prior to pretreatment at 35-50% dry matter. About 50 kg DM/h biomass was pretreated at temperatures from 170-200° C. with a residence time setting of 12-18 minutes. The biomass was loaded into the reactor using a sluice system and the pre-treated material unloaded using a sluice system. The pressure within the pressurized pre-treatment reactor corresponded to the pressure of saturated steam at the temperature used. The pretreated biomass was subject to solid/liquid separation using a screw press, producing a liquid fraction and a solid fraction having about 30% dry matter. The solid fraction was washed with about 3 kg water/kg dry biomass and pressed to about 30% dry matter again with 15-30% of the dissolved solids remaining in the solid fraction. Details concerning the pretreatment reactor and process are further described in Petersen et al. (2009).

Samples of solid fraction were collected after three hours of continuous pretreatment and samples were collected three times over three hours to ensure that a sample was obtained from steady state pretreatment. The solid fractions were analysed for carbohydrates according to the methods described in Sluiter et al. (2008) with an Ultimate 3000 HPLC system from Dionex equipped with a Rezex Monossacharide H+ Monosaccharide column.

The dry matter content and the amount of suspended solids was analysed according to the methods described in Weiss et al. (2009).

The severity of a pretreatment process is commonly described by a severity factor, first developed by Overend et al. (1987). The severity factor is typically expressed as a log value such that $\log(R0) = \text{reksp}((T-T_{ref})/14.75)$, where R0 is the severity factor, t is the residence time in minutes, T is the temperature and Tref is the reference temperature, typically 100° C. The severity factor is based on kinetics of hemicellulose solubilisation as 20 described by Belkecemi et al. (1991), Jacobsen and Wyman (2000) or Lloyd et al. (2003).

Solid fractions prepared and washed as described were analysed for xylan content according to the methods described by Sluiter et al. (2008) with a Dionex Ultimate 3000 HPLC system equipped with a Rezex Monossacharide H+ column from Phenomenex. The xylan content in the solid fraction produced and washed as described above is linearly dependent upon the severity factor log Ro for all the soft lignocellulosic biomasses tested, including wheat straw, corn stover, sugarcane bagasse, rape straw or EFB when pretreating by hydrothermal autohydrolysis. The definition of severity as the xylan content in a solid fraction prepared and washed as described above is transferable between pretreatment setups. Xylan number is the measured xylan content in the washed solid fractions, which includes some contribution from soluble material. The dependence of xylan number on pretreatment severity log(Ro) is shown in FIG. 1 for (A) wheat straw from the same area harvested in three different years (WS A, C and D), (B) two types of corn stover (CS B and D), (C) rape straw (RS), sugarcane bagasse (SCB) and empty fruit bunches (EFB) from palm oil processing. The lines are added as guide for the eye.

As shown, there exists a clear, negative linear correlation between xylan number and pretreatment severity for each of the tested biomass feedstocks pretreated by autohydrolysis. The lines serve as guides to the eye. As shown, different biomass feedstocks give rise to different linear relationships between xylan number and severity, even when comparing different harvest years of similar wheat strains.

Example 2

"Lignin Number" Characterization of Solid Fraction as a Measure of Pretreatment Severity Biomass feedstocks were pretreated, samples of solid fraction were prepared, and samples of liquid fraction and solid fraction obtained as described in Example 1. For each of the samples for which xylan number results were reported in Example 1, a separate determination of Klason lignin content was also made according to the method described in Sluiter et al. (2008). The Klason lignin determination included a measurement of all solids that were insoluble in 72% w/w sulphuric acid.

The dependence of lignin number on pretreatment severity log(Ro) is shown in FIG. 2 for (A) wheat straw from the same area harvested in three different years (WS A, C and D), (B) two types of corn stover (CS B and D), (C) rape straw (RS), sugarcane bagasse (SCB) and empty fruit bunches (EFB) from palm oil processing. The lines are added as guide for the eye.

As shown, there exists a clear, positive linear correlation between lignin number and pretreatment severity for each of the tested biomass feedstocks pretreated by autohydrolysis.

Example 3

Correlation of "Xylan Number" and "Lignin Number" with Enzymatic Digestibility Experiments were conducted in a 6-chamber free fall reactor working in principle as the 6-chamber reactor described and used in WO2006/056838. The 6-chamber hydrolysis reactor was designed in order to perform experiments with liquefaction and hydrolysis of pretreated biomass at solid concentrations above 20% DM. The reactor consists of a horizontally placed drum divided into 6 separate chambers each 24 cm wide and 50 cm in height. A horizontal rotating shaft mounted with three paddles in each chamber was used for mixing/agitation. A 1.1 kW motor was used as drive and the rotational speed is adjustable within the range of 2.5 and 16.5 rpm. The direction of rotation was programmed to shift every second minute between clock and anti-clock wise. A water-filled heating jacket on the outside enables control of the temperature up to 80° C.

The experiments used wheat straw pretreated by autohydrolysis to xylan numbers ranging from 5 to 16%. The biomass was cut and wetted to a DM of >35% and pretreated by steam at 170-190° C. for 12 min. The pretreatment was conducted in the Inbicon pilot plant in Skærbæk, Denmark. The pretreated biomass was separated into a washed solid fraction and a liquid fraction as described in Example 1.

The chambers of the 6 chamber reactor were filled with about 10 kg washed solid fraction with varying pretreatment severity and adjusted by water addition to 19-27% DM. The pretreated biomass was hydrolyzed at 50° C. and pH 5.0 to 5.3 using varying enzyme dosage of a commercially available cellulase preparation optimized for lignocellulosic biomass conversion and provided by NOVOZYMES™ under the trade name CTEC3™. The mixing speed was 6 rpm. The hydrolysis experiments were run for 100 hours.

HPLC samples were taken daily to follow the conversion of cellulose and hemicellulose and analysed for glucose, xylose and arabinose using a Dionex Ultimate 3000 HPLC system equipped with a Rezex Monosaccharide column with quantification through use of external standard.

The experiments were conducted according to a fractional factorial experimental design. In this way xylan number and enzyme dosage were varied simultaneously (N=18), and the results were connected and fitted by means of a mathematical model (linear with interactions) in order to estimate cellulose conversion using software MODDE™ from Umetrics. This model was then used for interpretations, predictions and optimizations.

FIG. 3 and FIG. 4 show cellulose conversion for pretreated wheat straw predicted by this model plotted as a function of xylan number and lignin number, respectively, fixed at 25% DM, pH 5 and a fixed enzyme dosage.

As shown, "xylan number" and "lignin number" measurements correlate with enzymatic digestibility in a manner that is approximately linear over the range shown.

Example 4

Determination of "Xylan Number" and "Lignin Number" Using NIR Spectra

Wheat straw was pretreated in Inbicon's demonstration plant in Kalundborg, Denmark, as described in (Larsen, Haven, & Thirup, 2012).

Pretreated biomass was separated into a solid fraction having between 18 and 28% DM and washed using a filter press to provide washed solid fractions comprising between 1.5 and 3.0% dissolved solids. After adjustment of the washed solid fraction to pH 5 using NaOH, a set of more than 400 samples of about 300 g each were obtained at a variety of pretreatment severities corresponding to a range of log Ro between about 3.4 and 4.1. Samples were obtained using a specially designed sampler in order to provide a representative sample of the pretreated biomass output stream. A sample of washed solid fraction is removed by a screw auger into a chamber comprising an NIR diffuse reflection probe. NIR absorbance spectra in the range 800 nm to 2500 nm were obtained in this sampling chamber using an FTPA2000-263 FT-NIR instrument from ABB (Q-interline). These online NIR measurements, that is, measurements made in sampling devices directly associated with the continuous pretreated biomass output stream, were stored for subsequent use. The physical samples from which online NIR measurements were obtained were then individually measured to determine NIR absorbance spectra in the range 800 nm to 2500 nm using an offline laboratory FT-NIR instrument, a Quant Q-interline (BOMEM, ABB).

The offline instrument had previously been calibrated to determine NIR spectral models for prediction of xylan number and lignin number in wheat straw pretreated as described. NIR spectra of more than 150 reference samples covering a range of pretreatment severities were determined. These same physical samples were used to determine total xylan and Klason lignin using the chemical measurements described by Sluiter et al. (2008).

Based on offline NIR spectra of the reference samples, and the results of the reference chemical analysis of these samples, multivariate calibration models were established for offline NIR determination of xylan number and lignin number, using Partial Least Squares (PLS) analysis well known in the art.

NIR spectra were adjusted prior to PLS calibration by taking the Savitzky-Golay second derivative. The Savitzky-Golay algorithm is based on a least squares linear regression fit of a polynomial around each point in the spectrum to smooth the data. Here a second order polynomial was used. The second derivative was then the second derivative of the fitted polynomial at each point. The algorithm includes a smoothing factor that determines how many adjacent variables will be used to estimate the polynomial approximation of the curve segment. Here 5 adjacent variables were used. Only the wavelength range 4800-9100 cm$^{-1}$ was used for the calibrations.

FIG. 5 shows representative examples of NIR spectra—raw spectra to the left and Savitzky-Golay second derivative pretreated spectra to the right.

The regression model was derived according to the fit:

$$Y = b_0 + b_1 X_1 + \ldots + b_k X_k + e$$

where the observed response value Y (e.g lignin number or xylan number) were approximated by a linear combination of the values of the predictors (the adjusted wavelength variables). The regression coefficients or "B-coefficients" of the determined combinations for xylan number and for lignin number are shown in FIG. 6 and FIG. 7 respectively.

These NIR spectral models were then applied to the online NIR measurements for randomly segmented cross validation against the xylan number and lignin number measures provided by the corresponding offline NIR measurements. The resulting plot showing a comparison of online NIR predictions versus the offline reference values for xylan number and for lignin number are shown in FIG. 8 and FIG. 9 respectively.

Table 1 shows the RMSEP (Root Mean Squared Error of Prediction), $R^2$ and number of used principal components for calibration of online NIR measurements of both xylan number and lignin number.

TABLE 1

The RMSEP (Root Mean Squared Error of Prediction), $R^2$ and number of used principal components for calibration of online NIR measurements of both xylan number and the lignin number.

|  | RMSEP | $R^2$ | #PC (principal components) |
|---|---|---|---|
| Xylan calibration | 0.83 | 0.69 | 10 |
| Lignin calibration | 1.22 | 0.71 | 9 |

Example 5

Feedback Control of Hydrothermal Pretreatment in Response to Online NIR Measurements of Xylan Number The temperature and residence time in the pretreatment reactor in Inbicon's demonstration plant in Kalundborg, Denmark, have since 2009 been feedback regulated from online and off-line measurements of the Xylan number in the washed solid fraction. See (Larsen, Haven, & Thirup, 2012). In this initial testing, feedback control was accomplished manually. Xylan number was measured by online and offline NIR measurements of the pretreated biomass output stream, which was separated to a washed solid fraction by a consistent method. Xylan number was measured approximately once every 4 hours, and either reactor dwell time or reactor temperature or both adjusted in such manner as to cause the pretreatment reactor to provide a "predetermined" set point xylan number level of 8. Steam temperature adjustments were typically +/−1° C. within the range 180 to 200° C., while reactor dwell time adjustments +/−1-5 minutes within the range 10 to 20 minutes.

FIG. 10 shows reactor temperature recorded over time during the period July to November, 2011, along with a moving average of xylan number measurements (nearest 4 measurements averaged) over the same time period. The indicated value of reactor temperature is adjusted to reflect the corresponding log Ro severity value where reactor dwell time was fixed at 15 minutes, in order to account for actual variations in reactor dwell time.

As shown, by feedback control of the pretreatment reactor based on measurements of xylan number in the pretreated biomass output stream, xylan number could be maintained within about +/−1 on the xylan number scale. This corresponds to control within about +/−1% in glucan conversion, as illustrated by FIG. 3. The importance of this kind of feedback control is dramatically illustrated by the shift in average reactor temperature observed where biomass feedstock was changed from 2010 to 2011 harvest years, as shown in FIG. 10. This shift of about 4° C. in reactor temperature relates to changes observed within a relatively homogenous biomass feedstock source, within a small geographic area. Such variability in feedstocks can be expected to be increased in larger scale facilities handling larger quantities of biomass, which will necessarily reflect greater genetic and geographic variability.

The description of embodiments and examples are exemplary only and not intended to limit the scope of the claims.

REFERENCES

Alvira, P et al., "Pretreatment technologies for an efficient bioethanol production process based on enzymatic hydrolysis: A review," Bioresource Technology (2010), 101: 4851.

Petersen, M et al., "Optimization of hydrothermal pretreatment of wheat straw for production of bioethanol at low water consumption without addition of chemicals," Biomass and Bioenergy (2009), 33:834.

Belkacemi, K., Abatzoglou, N., Overend, R. P., Chornet, E., 1991. Phenomenological Kinetics of Complex Systems: Mechanistic Considerations in the Solubilization of Hemicelluloses following Aqueous/Steam Treatments. *Ind. Eng. Chem. res.*, 30, 2416-2425.

Jacobsen, S. E., Wyman, C. E., 2000. Cellulose and Hemicellulose Hydrolysis Models for Application to Current and Novel Pretreatment Processes. *Applied Biochemistry and Biotechnology*, 84-86, 81-96.

Lloyd, T. A., 2003. Application of a Depolymerization Model for Predicting Thermochemical Hydrolysis of Hemicellulose. *Applied Biochemistry and Biotechnology*, 105-108, 53-67.

Overend, R. P., Chornet, E., 1987. Fractionation of lignocellulosics by steam aqueous pretreatments *Philos. Trans. R. Soc. Lond. A*, 321, 523-536.

Sluiter, A., Hames, B., Ruiz, R., Scarlata, C., Sluiter, J., Templeton, D., 2005. Determination of Sugars, Byproducts, and Degradation Products in Liquid Fraction Process Samples. NREL-Biomass Program.

Sluiter, A., Hames, B., Ruiz, R., Scarlata, C., Sluiter, J., Templeton, D., Crocker, D., 2006. Determination of Structural Carbohydrates and Lignin in Biomass. NREL-Biomass Program.

Alvira, P., et al., "Pretreatment technologies for an efficient bioethanol production process based on enzymatic hydrolysis: A review," Bioresource Technology (2010), 101: 4851

Knudsen, N., et al., "Possibilities and evaluation of straw pretreatment," 10th european biomass conference in Würzburg in 1998

Jeoh, T., et al., "Cellulase digestibility of pretreated biomass is limited by cellulose accessibility," Biotechnology and Bioengineering (2007), 98(1):112

Bura, R., et al., "Influence of xylan on the enzymatic hydrolysis of steam-pretreated corn stover and hybrid poplar," Biotechnol. Prog. (2009), 25:315

Kabel, M., et al., "Effect of pretreatment severity on xylan solubility and enzymatic breakdown of the remaining cellulose from wheat straw," Bioresource Technology (2007), 98:2034

Lindedam, J., et al., "Cellulosic ethanol: interactions between cultivar and enzyme loading in wheat straw processing," Biotechnology for Biofuels (2010), 3:25

Liu, L., et al., "Variability of biomass composition and rapid analysis using FT-NIR techniques," Carbohydrate Polymers (2010), 81:820

Weiss, N., et al., "Impact of corn stover composition on hemicellulose conversion during dilute acid pretreatment and enzymatic cellulose digestibility of the pretreated solids," Bioresource Technology (2010), 101:674

Gollapalli, L., et al., "Predicting digestibility of ammonia fiber explosion (AFEX)-treated rice straw," Applied Biochemistry and Biotechnology (2002), 98-100:23

Zhu, L., et al., "Multiple linear regression model for predicting biomass digestibility from structural features," Bioresource Technology (2010), 101:4971

Chandra, R., et al., "Substrate pretreatment: The key to effective enzymatic hydrolysis of lignocellulosics?," Adv. Biochem Engin./Biotechnol (2007), 108:67

Hames, B. et al., "Rapid biomass analysis: New tools for compositional analysis of corn stover feedstocks and process intermediates from ethanol production," Applied Biochem. and Biotechnol. (2003), 105-108:5

A. Sluiter, et al., "Determination of structural carbohydrates and lignin in biomass," US National Renewal Energy Laboratory (NREL) Laboratory Analytical Procedure (LAP) with issue date Apr. 25, 2008, as described in Technical Report NREL/TP-510-42618, revised April 2008

Perez, J. et al., "Effect of process variables on liquid hot water pretreatment of wheat straw for bioconversion to fuel-ethanol in a batch reactor," Journal of Chemical Technology and Biotechnology (2007), 82:929.

Weiss, N. et al., "Impact of corn stover composition on hemicellulose conversion during dilute acid pretreatment and enzymatic cellulose digestibility of the pretreated solids," Bioresource Technology (2010), 101:674.

Larsen, J., et al., "Inbicon makes cellulosic ethanol a commercial reality," Biomass and Bioenergy (2012), doi: 10.1016/biombioe.2012.03.033 (article in press)

The invention claimed is:

1. A method of processing lignocellulosic biomass comprising
    pretreating lignocellulosic biomass feedstock by continuous hydrothermal pretreatment in a pressurized reactor,
    measuring xylan number or lignin number in the output stream of said pretreated lignocellulosic biomass feedstock from the pretreatment reactor by measuring NIR spectra in the pretreated biomass output stream followed by correlating the measured NIR spectra to an NIR spectral model, and
    adjusting the pretreatment reactor conditions so as to maintain, in the output stream of said pretreated lignocellulosic biomass, a pre-determined level of measured xylan number or lignin number.

2. The method of claim 1 wherein NIR spectra is measured using NIR absorbance spectra in the range 800 nm to 2500 nm.

3. The method of claim 1 wherein lignocellulosic biomass feedstocks are pretreated at 25% dry matter (DM) or greater.

4. The method of claim 1 wherein lignocellulosic biomass is pretreated at pH between 2.5 and 8.

5. The method of claim 1 wherein pretreated lignocellulosic biomass is removed from the reactor by hydrocyclone.

6. The method of claim 1 wherein xylan number or lignin number is measured in whole slurry of pretreated lignocellulosic biomass.

7. The method of claim 1 wherein xylan number or lignin number is measured in washed solid fraction of pretreated lignocellulosic biomass.

8. The method of claim 1 wherein xylan number or lignin number is measured in unwashed solid fraction of pretreated lignocellulosic biomass.

9. The method of claim 1 wherein xylan number or lignin number is measured using online NIR measurements.

10. The method of claim 1 wherein the reactor conditions are adjusted over an interval of once every minute.

11. The method of claim 1 wherein adjusting the pretreatment reactor conditions comprises adjusting reactor temperature.

12. The method of claim 1 wherein adjusting the pretreatment reactor conditions comprises adjusting reactor dwell time.

13. The method of claim 1 wherein the lignocellulosic biomass is pretreated to severity log Ro between 3.2 and 3.9.

14. The method of claim 1 wherein xylan number is measured in a sample comprising more than 0.8% but less than 4% dissolved solids.

* * * * *